(12) United States Patent
Benk et al.

(10) Patent No.: US 10,695,407 B2
(45) Date of Patent: Jun. 30, 2020

(54) PROTECTIVE SOLUTION FOR PREVENTING OR REDUCING REPERFUSION INJURY OF THE BRAIN AND THE WHOLE BODY

(71) Applicant: ResuSciTec GmbH, Freiburg i.Br. (DE)

(72) Inventors: Christoph Benk, Freiburg (DE); Friedhelm Beyersdorf, Freiburg (DE); Georg Trummer, Freiburg (DE)

(73) Assignee: ResuSciTec GmbH, Freiburg i.Br. (DE)

( * ) Notice: Subject to any disclaimer, the term of this patent is extended or adjusted under 35 U.S.C. 154(b) by 314 days.

(21) Appl. No.: 14/902,196

(22) PCT Filed: Jul. 1, 2014

(86) PCT No.: PCT/EP2014/063905
§ 371 (c)(1),
(2) Date: Dec. 30, 2015

(87) PCT Pub. No.: WO2015/000871
PCT Pub. Date: Jan. 8, 2015

(65) Prior Publication Data
US 2016/0367643 A1    Dec. 22, 2016

(30) Foreign Application Priority Data

Jul. 5, 2013 (EP) ..................................... 13175243

(51) Int. Cl.
*A61K 38/38* (2006.01)

(52) U.S. Cl.
CPC ................................ *A61K 38/385* (2013.01)

(58) Field of Classification Search
None
See application file for complete search history.

(56) References Cited

U.S. PATENT DOCUMENTS

| 5,552,267 | A  | * | 9/1996  | Stern    | A01N 1/0226 |
|           |    |   |         |          | 435/1.1     |
| 7,288,551 | B1 | * | 10/2007 | Masters  | A01N 1/02   |
|           |    |   |         |          | 435/1.2     |
| 8,012,677 | B2 | * | 9/2011  | Steen    | A01N 1/02   |
|           |    |   |         |          | 435/1.2     |
| 9,131,677 | B2 |   | 9/2015  | Megson   |             |
| 2009/0305222 | A1 |   | 12/2009 | Megson |             |
| 2011/0008763 | A1 | * | 1/2011 | Lee | A01N 1/0221 |
|           |    |   |         |          | 435/1.2     |
| 2011/0300237 | A1 |   | 12/2011 | De Groot et al. | |
| 2012/0203158 | A1 |   | 8/2012  | Beyersdorf | |

FOREIGN PATENT DOCUMENTS

| EP | 1 362 511 A1 | 5/2003 |
| WO | WO 2008/001096 A2 | 1/2008 |
| WO | WO 2011/008695 A2 | 1/2011 |
| WO | WO 2011/045011 A1 | 4/2011 |

OTHER PUBLICATIONS

Smulowitz ("Ex vivo cardiac allograft preservation by continuous perfusion techniques" ASAIO Journal 2000).*
Sunamori et al. ("The use of nondepolarizing cardioplegic solution for cardiac preservation has a beneficial effect on the left ventricular diastolic function" Tranpl Int (2001) 14:72-79).*
Salameh et al. (Strategies for pharmacological organoprotection during extracorpeal circulation targeting ischemia-reperfusion injury ; Frontiers in Pharmacology, Dec. 2015, vol. 6).*
Kalogeris et al. (Cell Biology of Ischemia/Reperfusion Injury; Int. Rev. Cell Mol Biol. 2012; 298; 229-317).*
PCT/EP2014/063905—International Search Report, dated Oct. 7, 2014.
PCT/EP2014/063905—International Written Opinion, dated Oct. 7, 2014.
PCT/EP2014/063905—International Preliminary Report on Patentability, dated Jan. 5, 2016.
Haidekker, Mark, et al., "A Novel Approach to Blood Plasma Viscosity Measurement Using Fluorescent Molecular Rotors", American Journal of Physiology-Heart and Circulatory Physiology, May 1, 2002, pp. H1609-H1614, vol. 282, No. 5.
Trummer, Georg, et al., "Suscessful Resuscitation After Prolonged Periods of Caridac Arrest: A New Field in Cardiac Surgery", The Journal of Thoracic and Cardiovascular Surgery, May 2010, pp. 1325-1332, vol. 139, Issue 5. (Abstract only).
Suarez, Jose, et al. "Treatment of Subarachnoid Hemorrhage with Human Albumin: ALISAH Study. Rationale and Design", Neurocritical Care, Jun. 10, 2010, pp. 263-277, vol. 13, No. 2.

* cited by examiner

*Primary Examiner* — James H Alstrum-Acevedo
*Assistant Examiner* — Tara L Martinez
(74) *Attorney, Agent, or Firm* — Curatolo Sidoti Co., LPA; Salvatore A. Sidoti; Floyd Trillis, III

(57) ABSTRACT

The present invention relates to a protective solution for preventing or reducing reperfusion injury of the brain which contains magnesium ions and which has an osmolality of 350 to 600 mOsm/L, a pH value of 6.8 to 7.8 and albumin in an amount of 1 to 20% by weight.

27 Claims, No Drawings

PROTECTIVE SOLUTION FOR PREVENTING OR REDUCING REPERFUSION INJURY OF THE BRAIN AND THE WHOLE BODY

CROSS REFERENCE TO RELATED APPLICATIONS

This application is a national stage application of International Application No. PCT/EP2014/063905, filed 1 Jul. 2014, which claims priority from European Patent Application No. 13175243.8, filed 5 Jul. 2013, from which applications priority is claimed, and which are hereby incorporated herein by reference in their entireties.

Sudden circulatory arrest is frequent with an incidence of 60/100000 residents in the European Union. Cardiopulmonary resuscitation (CPR) including external chest massage, defibrillation, mechanical ventilation and drug therapy is the established way of treatment. However despite increasing efforts in training for medical staff and potential bystanders, improved equipment and extensive interdisciplinary guidelines, CPR remains a difficult and somewhat improvised task. Furthermore, the outcome regarding survival and neurologic recovery is not satisfying: Mortality rates of >70% are reported in patients undergoing in-hospital CPR which much higher rates in out-of-hospital scenarios. Beyond that, cerebral damage is frequent in the rare case of survival.

Trummer et al., The Journal of Thoracic and Cardiovascular Surgery, May 2010, p. 1325-1332 report the successful resuscitation after prolonged periods of cardiac arrest. According to this report it was possible to resuscitate in an animal model using pigs up to 15 minutes after cardiac arrest. In the experiments extracorporeal blood circulation was established using Ringer solution together with heparin as priming solution.

It is an object of the present invention to provide protective solutions which can be used in the resuscitation process after cardiac arrest. It is desirable to keep the damages in particular of the brain at the lowest possible level. It has been observed in many cases wherein patients have been resuscitated after a longer period after cardiac arrest that substantial damages of the brain occurred. Such damages had the effect that the persons were severely compromised in mental regard and such patients could not return to normal life.

Protective solutions are disclosed herein which can be preferably used in resuscitation proceedings which are in more detail described e.g. in WO 2011/045011. Within a relatively short period of time after cardiac arrest, the circulation of blood has to be re-established. When cardiac arrest occurs in a hospital, for example in the course of surgical treatments of the heart, the conditions are better controllable compared to cases where sudden cardiac arrest occurs outside of the hospital. There is usually a delay of time until doctors and bystanders can re-establish the blood circulation. The organ which is most seriously compromised by cardiac arrest is the brain. The protective solutions disclosed herein prevent or reduce damages which are caused by the restart of the blood circulation after cardiac arrest.

Up to date, it is generally accepted that normal cerebral and myocardial function can only recover when conventional CPR is employed within the first 3 to 5 minutes after circulatory standstill. Therefore, since time is the most important factor in determining patient outcomes after CPR, every attempt is made to start CPR as soon as possible after cardiac arrest to avoid cerebral damage after resuscitation.

However from a pathophysiological point of view, circulatory standstill following cardiac arrest may be interpreted as a whole-body ischemia followed by reperfusion injury when the blood supply is re-established. This phenomenon is known as an "ischemia-reperfusion injury" in the tissue of certain organs. However these organs can be salvaged for much longer intervals if the initial reperfusion after a significant ischemic insult is controlled in terms of the conditions of reperfusion (pressure, flow, temperature) and the reperfusate's composition. The beneficial effects of this treatment regimen have been shown in cardiac muscle, skeletal muscle, liver, lung and renal tissue.

Assuming that a severe ischemia-reperfusion injury of the whole body and brain after circulatory arrest is the underlying cause of morbidity and mortality after CPR, special attention was given to the conditions of reperfusion of the whole body after CPR. The option to connect the patient via cannulation of arterial and venous vessels to an extracorporeal-life-support-system (ECLS) with subsequent stabilization using extracorporeal circulation has been demonstrated to be a useful tool to improve survival after CPR. Since restoration of circulation and a sufficient blood supply to the organs, especially the brain, are major aspects regarding CPR, the use of ECLS during and after CPR potentially enables control of reperfusion conditions in terms of blood pressure, -flow, and the reperfusate. However, efficient conditions for whole-body reperfusion after normothermic cardiac arrest have not yet been defined.

Although it is the goal in resuscitation to avoid severe damages of the brain also other essential organs should not be fatally affected. In resuscitation proceedings care has to be taken that essential organs like in particular heart, liver, lung and kidney are not damaged to such an extent that the patient cannot survive the resuscitation. Since the best conditions for each organ may not be identical, sometimes the best compromise has to be selected which avoids severe damages of the brain on the one hand and irreversible damages of other essential organs like heart or lung on the other hand.

Within an extended series of animal experiments the relevance of these conditions was explored in an established porcine model. The results obtained therewith allow a reliable extrapolation to humans. One major object of this research is to provide a controlled perfusion of the whole body with priority for the demand of, the most sensitive organ, the brain. As described above, the ischemia-reperfusion injury, expressed as the extent of cerebral edema, should be limited as far as possible. Beyond the definition of physical conditions of reperfusion (temperature, blood pressure/flow) the composition of the reperfusate is subject of the present disclosure. In preferred embodiments hypocalcemia, hypermagnesemia and hyperosmolarity are relevant aspects to avoid edema in the reperfused tissue. The protective solutions described herein are also designated as priming solutions.

Without wishing to be bound to a theory, the use of these elements in a modified reperfusate is based on the following considerations:

One main aspect of the priming solution is hyperosmolarity. Osmosis occurs when a substance in solution crosses a membrane from an area of low concentration to an area of higher concentration in order to establish equilibrium. The concentration of particles dissolved in solution expressed as mole of solute per liter of solvent is referred to as "osmolality". In human plasma, the concentration of dissolved particles is about 0.290 mol. Therefore, its osmolality is 290 mOsm/L. The range of normal human plasma extends usually from about 250 to 310 mOsm/L.

Water flows from an area of low osmolality to an area of high osmolality at a rate directly proportional to the difference (radiant) in osmolality until equilibrium is reached. Solutions containing the same concentration of particles as blood are iso-osmotic (isotonic). In medicine a 0.9% sodium chloride solution which is iso-osmotic with blood and the venous endothelium is frequently used. Solutions with a lower osmolality (a lower concentration of the solved particles) are designated as hypotonic. Solutions with a higher osmolality than that of normal saline solution (0.9% sodium chloride) are designated as hypertonic or hyperosmolaric.

The protective solutions of the present invention are hyperosmolaric and have an osmolality ranging from 300 to 700 mOsm/L. A preferred range is 400 to 600 mOsm/L and particulary preferred is an osmolalilty of 440 to 550 mOsm/L. All particles dissolved in solution contribute to the osmolality.

One preferred component for increasing the osmolality of the protective solutions disclosed herein is albumin, preferably human albumin. Human-albumin was chosen as a basic component of the priming solution in order to generate a hyperosmolaric reperfusate. The comparable high molecular-mass of albumin potentially reduces the transfer of these molecules in the extravasal space and potentially binds intracellular fluid avoiding cellular edema.

In addition to human-albumin, the hyperosmotic properties of sugar alcohols, like mannitol can be used as a useful adjunct of the priming solution. In other embodiments it is possible to use also other substances to increase the osmolality. It has, however, to be considered that some of such components do also have side-effects when used as infusion solutions. Mannitol has, for example, an diuretic effect. Other suitable components are sugars such as e.g. glucose. When selecting other components, undesired side effects have to be avoided.

A further important aspect of the protective solutions described herein is the increased content of magnesia ions in the solution. It is believed that the high concentration of magnesia ions ($Mg^{2+}$) has protective effects in particular with respect to the prevention or reduction of damages caused by the reperfusion injury. Cytoprotective effects of hypermagnesemia have been described in the respiration of isolated heart mitochondria. Furthermore, platelet aggregation may be decreased with potential effects on the "No-reflow" phenomenon which is another symptom of the reperfusion injury. Therefore preferably magnesium is added to the priming solutions described herein. $Mg^{2+}$ ions can be introduced into the solution in the form of a suitable salt. One preferred component contributing to the high concentration of $Mg^{2+}$ is magnesium citrate. In this preferred embodiment the citrate anion has further advantageous properties as described below. Other preferred sources of $Mg^{2+}$ ions are magnesium sulphate or magnesium aspartate.

Since ischemia causes a failure of the energy dependent and cell-membrane based $Na^+/Ca^{2+}$ antiporter, the calcium concentration in the cytosol is increased excessively with subsequent accumulation of fluid within the cell. This fluid increase is synonymous with an edema of the cell finally leading to malfunction and potentially terminal failure of the cell. Therefore the reduced supply of calcium to the cell limits this effect. The reduction of the calcium content is reached by adding magnesium citrate or sodium-citrate to the priming solution. Alternatively, other chelating agents, such as e.g. 2,3-dimercapto-1-propane sulfonic acid (DMPS), alphalipoic acid (ALA) or ethylenediamine tetraacetic acid or methylamine can be used. The selection of the suitable chelating agent depends on the other components of the solution. Chelating agents which bind to $Ca^{2+}$ better than $Mg^{2+}$ are particularly preferred.

Another preferred component of the protective solution is lidocaine (2-diethylamino-N-(2,6-dimethylphenyl)acetamide). Lidocaine is available e.g. under the trademark Xylocaine and it is well known as a locally acting anaestheticum and antiarrhythmic agent.

In a preferred embodiment the protective solution comprises a high-dosage of Lidocain. Dosages range from 1 to 20 mg/kg body weight, more preferred 5 to 15 mg Lidocain per kg body weight of the patient to be treated, and particularly preferred around 10 mg/kg body weight is added to the priming solution. The amount of lidocaine present in the protective solution depends somewhat on the bodyweight of the patient to be treated.

Usually, the protective solution has a concentration of 0.05-1.0 g per l of solution. In more preferred embodiments, the lidocaine content ranges from 0.1-0.7 g per l solution. Even more preferred is an amount of 0.3-0.7 g per l solution. Since the body weight of the patient in an emergency case is not known the concentration of Lidocain can be calculated on an average body weight of e.g. 70 kg. Lidocain causes a blockage of the voltage-gated sodium channels finally leading to a stabilization of the cell membrane. This effect is beneficial in myocardial cells and neurons. Therefore Lidocain is a preferred component of the priming solution.

A further preferred adjunct of the priming solution is heparin. Heparin is used in order to provide sufficient anticoagulation, which is necessary to run the extracorporal circulation. Since many patients are not heparinized at the time of CPR or the coagulation status is not clear, the addition of this drug in the priming is conceivable.

In a preferred embodiment the protective solution for preventing or reducing reperfusion injury of the brain, has an osmolality of 350 to 600 mOsm/L, a pH value of 6.8 to 7.8, preferably 7.4 to 7.6. The physiological pH value of the human body is about pH 7.4. In a particularly preferred embodiment of the present invention the protective solutions disclosed herein have a somewhat lower pH value. It is therefore preferred to use a pH value of about 7.0 to 7.4 which lowers the pH value in the body.

For the maintenance of the pH value the protective solutions disclosed herein may also contain a buffering agent to allow an alcalotic pH of the solution at certain times of the perfusion process in order to counteract cell acidosis. A suitable buffering agent may be a phosphat, hydrogen phosphate system or a bicarbonate buffering system. Such buffer may be administered in a dosage of 0.1 mmol kg body weight and hour up to 3 mmol kg body weight and hour. The concentration of the buffering agent comprises all ions which may contribute to the buffering effect. In a phosphate buffering solution all phosphate ions ($PO_4^{3-}$, $HPO_4^{2-}$, $H_2PO_4^-$ and $H_3PO_4$) are taken into account in the calculation of the concentration of the buffering agent.

One of the components which contributes mostly to the hyperosmolality of the protective solution is albumin whereby human serum albumin is preferably used. Albumin is added to the protective solution in an amount of 1-20%, preferably 2-15% and more preferably 5-10% by weight based on solution. Albumin is usually available as solution with a high concentration of albumin, for example 20% human albumin in solution. Such solution with a high concentration of albumin is used for the preparation of the protective solution. Although albumin from other sources can also be used it is preferred to utilize human serum albumin since this material is available in large quantities. The human serum albumin to be used must be specifically prepared for human application. This means it must be free of contaminating viruses or other undesirable traces of toxic components.

In another embodiment, the protective solution contains also a further sugar alcohol. A preferred sugar alcohol is mannitol. It is, however, also possible to use erythritol.

It is an essential aspect of the present invention that the protective solution contains a high content of magnesium ions. The concentration of magnesium ranges from 0.1-15 mmol/l, preferably from 1.0-8.0 and more preferred from 1.5-4.5 mmol/l.

Another aspect of the protective solution is that the solution should be essentially free from calcium ions. In order to remove the calcium contained within the blood vessels, the protective solution contains a chelating agent. A preferred chelating agent is citrate. Citrate may be present in an amount of 0.1-20 mmol/l, preferably in an amount from 1.0-5.0 mmol/l. It is possible in a particularly preferred embodiment that the protective solution is prepared by using magnesium citrate in order to achieve a high concentration of magnesium and to introduce the citrate anions into the solution without counterions which might be disturbing the effect of the protective solution.

In another preferred embodiment the protective solution contains a substantial amount of heparin. Preferably, the heparin concentration ranges from 5000 to 50,000 IU per liter of solution, more preferred is a range of 15,000-40,000 IU per liter of solution and particularly preferred is a range of 20,000-30,000 IU per liter of solution.

An important aspect of the present invention is the viscosity of the protective solutions disclosed herein. In the resuscitation proceedings wherein the protective solutions (priming solutions) are used, the solution and the mixture of the solution and the blood of the patient have to be pumped through the body of the patient and through the used machine. The viscosity of the solution plays therefore an essential role. Viscosities of mixed solutions are difficult to describe precisely. Moreover, the viscosity is dependent on the temperature of the solution. It is essential that the protective solution described herein has a viscosity of less than 3 mPas at 37° C. and less than 5 mPas at 32° C. When the protective solutions are mixed with human blood the viscosity of the protective solution should be less than 4 mPas at 37° C. and less than 6 mPas at 32° C. The viscosity is determined by methods well-known to the person skilled in the art. One very common method to measure the viscosity is a Brookfield viscometer. Alternatively, however, the viscosity can also be measured by capillary viscometer or rotational viscometer. For the measurement of blood plasma a specialized capillary viscometer (hardness viscometer) has been recommended. Other methods are for example described in Haidekker et al., Am J Physiol Heart Circ Physiol, 2002, H1609-H1614).

The protective solutions disclosed herein are preferably used for the prevention or reduction of reperfusion injury of the brain which potentially occurs after cardiopulmonary resuscitation. The term cardiopulmonary resuscitation comprises events which may occur in the hospital, e.g. heart surgery or which may occur spontaneously in daily life and also outside of a hospital, e.g. after myocardial infarction or spontaneous ventricular fibrillation.

In a particularly preferred embodiment, the protective solution for reducing reperfusion injury of the brain is used in a device which is described in detail in WO 2011/04011.

A preferred protective solution contains lidocaine in an amount of 0.05-1.0 g per l of solution, a sugar alcohol in an amount of 1.0-50 g/l, whereby the sugar alcohol is preferably mannitol, magnesium which is present in a concentration of 1.0 to 15 mmol/l, 5000 to 50,000 IU heparin/l solution, and citrate ions in an amount of 20 to 100 mmol/l solution.

The protective solution is preferably used in the prevention or reduction of reperfusion injury of the brain after cardiopulmonary resuscitation.

In another preferred embodiment the protective solution is used in the prevention or reduction of reperfusion injury of the brain after cardiopulmonary resuscitation with a solution containing 0.1-25.0 mmol potassium per l of solution. In some embodiments it may be preferable to have a concentration of more than 8 mmol/l potassium in the solution. In such embodiments the concentration of potassium is 8 to 25 mmol potassium per liter of solution. The effect of the high concentration of potassium is that the cardiac defibrillation can be avoided or performed less frequently. By adding potassium to the solution the electric and consecutive the muscular activity of the heart is reduced to nearly zero. The advantage thereof is that the substrate and energy consuming process of ventricular fibrillation may be terminated. That means that after replenishment of substrates heart beating can be better initiated. Furthermore, the risk of dislocation of the inserted cannulas during potential defibrillation is decreased.

In a further embodiment the protective solution may contain norepinephrin in a concentration of 0.05 µg-0.5 µg norepinephrin per kg of the patient to be treated. Since the solutions are prepared in advance the final concentration in the protective solution may range from about 1 to 100 mg norepinephrin per liter of solution.

Cyclosporin attenuates the opening of the mitochondrial permeability transition pore and stabilizes the inner mitochondrial membrane in ischemic cardiomyocytes. Thereby cycolsporin A is a preferred component of the protective solution. In a further embodiment the protective solution may contain a concentration of 1.0-17.5 mg cyclosposrin A per kg of the patient to be treated. More preferred is a range of 2.5-15.0 per kg of the patient and particulary preferred is a range of 4.0-12.0 cyclosporine A per kg of the patient. The solution may therefore contain from 50 mg to 1300 mg Cyclosporin per liter of solution, preferably from 250 mg to 850 mg Cyclosporin per liter of protective solution.

An especially preferred priming solution is prepared by using:

| | |
|---|---|
| Human albumin 20% | 500 ml |
| Mannitol 20% | 250 ml |
| Sodium-Citricum 3.13% | 250 ml |
| Xylocain 2% | 25 ml |
| Magnesium 10% | 20 ml |
| Heparin | 15000 IE |

Lab analysis reveals the following chemical composition of a particularly preferred priming solution.

| Potassium mmol/l | Sodium mmol/l | Chlorid mmol/l | Calcium mmol/l | Magnesium mmol/l | Glucose mg/dl | Osmolality mosm/kg |
|---|---|---|---|---|---|---|
| 1 | 139.3 | 30.4 | 0.36 | 6.0 | <1.0 | 527 |

Although it is desired to keep the content of calcium as low as possible the final solution may contain some calcium which is usually brought into the solution as undesired impurity. Since human albumin is obtained from blood it may happen that traces of calcium are introduced into the solution as impurity. The content of calcium should, however, be lower than 0.5 mmol/l.

This priming solution is used to moisten, flush and de-air the extracorporeal circuit before the patient is connected to a device which is described for example in WO 2011/045011. After connection with the patient and the start of the blood pump the priming solution is mixed with the returning blood of the patient and reinfused in the patient via the arterial line. Dependent on the analysis of the returning blood, the reinfused blood is modified. Part of this modification may be the addition of drugs via a dosage-system which is part of our ECLS. The dosage system consists of a main-line which is continuously flushed with priming solution or any other intravenous crystalloid or colloid solution. Drugs may be added via separate side lines to the main line in dependence on the specific requirement of the patient. Therefore one can describe a dynamic drug composition at the end of the main line of the dosage system.

EXAMPLE 1

The protective solution was tested in an animal model. For the experiments a pig model was used which is described in detail in Trummer et al., Journal of Thoracic and Cardiovascular Surgery (2010), p. 1325 ff, to which we refer explicitly. In the experiments pigs having a weight of about 55 kg were anaesthesized with propofol. Anaesthesia and muscle paralysis was maintained with fentanyl. Two incisions were made for vascular access. During the experiment systemic blood pressure was monitored, cardiac arrest was induced by ventricular fibrillation and cardiac arrest was maintained for 20 minutes. After 20 minutes resuscitation was initiated by using different priming solutions. After treatment the animals were monitored for seven days. Thereafter euthanasia was performed. The brain was removed immediately thereafter and stored in formaline solution for histologic examination.

The neurological status of the test animals was assessed before anaesthesia and every 24 hours after cardiopulmonary resuscitation. The neurological examination consisted of five test aspects which are summarized below:
A. Central nerve function (0-100 points): pupil size (0-10); eye position (0-10); light, lid, and corneal reflex (each 0-10); ciliospinal and oculocephalic reflex (each 0-10); auditory and gag reflex (each 0-10); carinal reflex (0-10)
B. Respiration (0-100 points): normal (0), hyperventilation (25), abnormal (50), absent (100)
C. Motor sensory function (0-100 points): stretch reflex (0-25), motor response to pain (0-25), positioning (0-25), muscle tonus (0-25)
E. Level of consciousness (0-100 points): normal (0), cloudy (30), delirium (45), stupor (60), coma (100)
F. Behavior (0-100 points): drinking, chewing, sitting, and standing (each 0-15); walking (0-40)

The total score is the sum of all sections (0, normal; 500, brain death). Numbers in parentheses indicate scores for each parameter.

The pigs were divided into four groups whereby one control group and three test groups were used.

For the control group as priming solution a Ringer solution was used. The animals were treated as described in Trummer et al. (Journal of Thoracic and Cardiovascular Surgery, 2010, pp 1325-1332). The time period between cardiac arrest and cardiopulmonary resuscitation was 15 minutes in the control group.

In order to demonstrate that the time period between cardiac arrest and resuscitation can be extended by the protective solutions disclosed herein, the time span between cardiac arrest and resuscitation was 20 minutes for test groups 1-3. The difference of 5 minutes is extraordinarily important since very often, despite best organizations, more time is needed until the resuscitation action can start.

As solutions according to the invention three test solutions 1, 2 and 3 were used.

Test solution 1 had an osmolality of 440 mosm/l. It was a solution containing in addition to mannitol, lidocaine also human albumin. The animals were treated hypothermally aiming a body temperature of 32° C. for 30 minutes.

Test solution 2 had an osmolality of 550 mosm/l. It contained human albumin, mannitol, lidocaine, high concentrations of magnesium and sodium-citricum. The animals were treated hypothermally aiming a body temperature of 32° C. for 30 minutes.

Test solution 3 had an osmolality of 550 mosm/l. It contained human albumin, mannitol, lidocaine, high concentrations of magnesium and sodium-citricum. Furthermore, the concentration of natrium was lowered. The animals were treated under normal thermal conditions. No attempts were made to control the temperature in this group. The body temperature of the pigs remained at ~36° C.

The test results are provided in the following Table:

| Time between cardiac arrest and resuscitation | test solutions | total number of pigs used in this experiment | pigs showing good results on the neurological deficit score |
|---|---|---|---|
| 15 minutes | control 1 | 6 | 4 |
| 20 minutes | test solution 1 | 9 | 6 |
| 20 minutes | test solution 2 | 9 | 6 |
| 20 minutes | test solution 3 | 10 | 9 |

The experiments clearly show that the protective solutions described herein do substantially reduce
a) the mortality in these animals and
b) damages of the brain and allow a recovery after an incredibly long time period between cardiac arrest and cardiopulmonary resuscitation (20 minutes). The neurologic recovery has been quantified with the aforementioned Scoring system (NDS). "Good recovery" includes full consciousness, standing up, walking, eating and drinking of the animals.

The comparative example shows clearly that the test solutions disclosed herein allow a prolongation of the time period between cardiac arrest and the start of the resuscitation proceedings. The results of the neurological deficit core suffered in the control after 15 minutes was well comparable to the test solution. The important difference is, however, the time difference between 15 minutes and 20 minutes. Furthermore, the experiment shows that a hypothermal treatment further improves the results.

With the control solutions it was also possible to avoid brain damage in several cases. The longer the period of time is after which the animals used in the experiments did not suffer severe neurological damages, the better such solutions can be used in human beings in order to avoid damages of the brain in cases of cardiogenic shock, severe circulatory failure or cardiopulmonary resuscitation.

The invention claimed is:

1. A protective solution for reducing reperfusion injury of the brain comprising magnesium ions and albumin in an amount of 1 to 20% by weight, wherein said protective solution has an osmolality of 440 to 550 mOsm/L and a pH value of 7.5 to 7.8.

2. The protective solution according to claim 1, characterized in that the albumin is human serum albumin.

3. The protective solution according to claim 2, characterized in that it contains lidocaine in an amount of 0.05-1.0 g per l of solution.

4. The protective solution according to claim 3, characterized in that it contains a sugar alcohol in an amount of 1.0-50 g/l.

5. The protective solution according to claim 2 characterized in that it contains a sugar alcohol in an amount of 1.0-50 g/l.

6. The protective solution according to claim 5, characterized in that it contains mannitol in an amount of 1.0-50 g/l.

7. The protective solution according to claim 2, characterized in that it contains citrate ions in a concentration of 20 to 100 mmol/l solution.

8. The protective solution according to claim 1, characterized in that it contains lidocaine in an amount of 0.05-1.0 g per l of solution.

9. The protective solution according to claim 8, characterized in that it contains 10,000 to 50,000 IU heparin per liter of solution.

10. The protective solution according to claim 8, characterized in that it contains citrate ions in a concentration of 20 to 100 mmol/l solution.

11. The protective solution according to claim 1, characterized in that it contains a sugar alcohol in an amount of 1.0-50 g/l.

12. The protective solution according to claim 11, characterized in that the sugar alcohol is mannitol.

13. The protective solution according to claim 12, characterized in that it contains 10,000 to 50,000 IU heparin per liter of solution.

14. The protective solution according to claim 12, characterized in that it contains citrate ions in a concentration of 20 to 100 mmol/l solution.

15. The protective solution according to claim 11, characterized in that it contains citrate ions in a concentration of 20 to 100 mmol/l solution.

16. The protective solution according to claim 1, characterized in that the magnesium is present in a concentration of 0.1 to 15 mmol/l.

17. The protective solution according to claim 16, characterized in that it contains citrate ions in a concentration of 20 to 100 mmol/l solution.

18. The protective solution according to claim 1, characterized in that it contains 10,000 to 50,000 IU heparin per liter of solution.

19. The protective solution according to claim 18, characterized in that it contains citrate ions in a concentration of 20 to 100 mmol/l solution.

20. The protective solution according to claim 1, characterized in that it contains citrate ions in a concentration of 20 to 100 mmol/l solution.

21. The protective solution according to claim 1, characterized in that it contains Cyclosporin in an amount of 50 mg to 1300 mg per liter of protective solution.

22. The protective solution according to claim 21, characterized in that it contains citrate ions in a concentration of 20 to 100 mmol/l solution.

23. The protective solution according to claim 1, wherein the solution comprises less than 0.5 mmol/l calcium ions.

24. The protective solution according to claim 1, wherein the solution comprises magnesium which is present in a concentration of 1.0 to 15 mmol/l, lidocaine in an amount of 0.05-1.0 g per l of solution, a sugar alcohol in an amount of 1.0-50 g/l, 5000 to 50,000 IU heparin/l solution, and citrate ions in an amount of 20 to 100 mmol/l solution.

25. The protective solution according to claim 1, wherein said protective solution has an osmolality of 440 to 500 mOsm/L.

26. A method for reducing reperfusion injury of the brain after cardiopulmonary resuscitation comprising administering a protective solution comprising magnesium ions and albumin in an amount of 1 to 20% by weight, wherein said protective solution has an osmolality of 440 to 550 mOsm/L and a pH value of 7.5 to 7.8.

27. The method of claim 26, wherein said protective solution further contains 0.1-25.0 mmol potassium per liter of solution.

* * * * *